(12) United States Patent
Ichinose et al.

(10) Patent No.: US 6,627,201 B2
(45) Date of Patent: Sep. 30, 2003

(54) COMPOSITION FOR DRINKING/EATING AND BEVERAGE/FOOD

(75) Inventors: Takayoshi Ichinose, Kyoto (JP); Yo Naoki, Kyoto (JP); Toru Mizoguchi, Kyoto (JP); Yasuaki Nanba, Hyogo (JP); Hitoshi Kubota, Hokkaido (JP)

(73) Assignee: Kabushiki Kaisha Sun Chlorella (JP)

( * ) Notice: Subject to any disclaimer, the term of this patent is extended or adjusted under 35 U.S.C. 154(b) by 0 days.

(21) Appl. No.: 10/112,899

(22) Filed: Apr. 1, 2002

(65) Prior Publication Data
US 2003/0017249 A1 Jan. 23, 2003

(30) Foreign Application Priority Data
Apr. 3, 2001 (JP) .......................... 2001-104642

(51) Int. Cl.⁷ .................. A61K 35/84; A61K 35/78; A61K 35/80
(52) U.S. Cl. .................. 424/195.15; 514/8; 514/54; 514/55; 424/195.17
(58) Field of Search ................ 514/8, 54, 55; 424/195.15, 195.17

(56) References Cited

U.S. PATENT DOCUMENTS 4,822,612 A    4/1989   Shinpo

FOREIGN PATENT DOCUMENTS

| JP | 55-74797 | 6/1980 |
| JP | 55-108292 | 8/1980 |
| JP | 62-19528 | 1/1987 |
| JP | 64-66127 | 3/1989 |
| JP | 64-67194 | 3/1989 |
| JP | 64-67195 | 3/1989 |
| JP | 2-78630 | 3/1990 |
| JP | 11-32723 | 2/1999 |
| JP | 2000-279128 | 10/2000 |
| JP | 2001-61441 | 3/2001 |
| JP | 2001-89388 | 4/2001 |
| JP | 2002-145796 | 5/2002 |

*Primary Examiner*—Raymond Henley, III
*Assistant Examiner*—Donna Jague
(74) *Attorney, Agent, or Firm*—McGlew and Tuttle, P.C.

(57) ABSTRACT

The composition for beverages/food of the present invention is a mixture of the AGARICUS BLAZEI MURRILL fruiting body and mycelium extract in a ratio by dry weight of 1:0.05 to 1:0.5, and chlorella growth factor. The ratio by dry weight of said mixture and chlorella growth factor is 1:0.05 to 1:1.

20 Claims, 2 Drawing Sheets

COMPOSITION FOR DRINKING/EATING AND BEVERAGE/FOOD

BACKGROUND OF THE INVENTION

1. Field of the Invention

The present invention relates to a composition for drinking/eating comprising a mixture of the AGARICUS BLAZEI MURRILL fruiting body and mycelium extract, and chlorella growth factor, which composition is excellent in antitumor effects, and a beverage/food containing said composition.

2. Description of the Prior Art

AGARICUS BLAZEI MURRILL reportedly possesses antitumor activity, and the antitumor substance in AGARICUS BLAZEI MURRILL has been the subject of various patent applications (Japanese Patent Unexamined Publication Nos. 74797/1980, 67194/1989, 67195/1989, 108292/1980, 66127/1989, and 78630/1990).

However, the antitumor substance which was the subject of these patent applications is required to be more potent in terms of antitumor activity, and is not capable of fully exhibiting the biological activity of AGARICUS BLAZEI MURRILL other than the antitumor activity.

The present invention was developed in view of the above problems in the prior art. Accordingly, the object of the present invention is to provide a composition for drinking/eating and a beverage/food, which are outstanding in antitumor effects, which are safe for beverage/food use, and which more effectively exhibit the biological activity of AGARICUS BLAZEI MURRILL as compared to AGARICUS BLAZEI MURRILL as a single substance.

SUMMARY OF THE INVENTION

For accomplishing the above object, the composition for beverages/food of the present invention comprises a mixture of the AGARICUS BLAZEI MURRILL fruiting body and mycelium extract in a ratio by dry weight of 1:0.05 to 1:0.5, and chlorella growth factor, wherein the ratio by dry weight of said mixture and chlorella growth factor is 1:0.05 to 1:1.

The beverage/food of the present invention contains the composition for drinking/eating described above.

The composition for drinking/eating of the present invention and the beverage/food of the present invention have outstanding antitumor effects, are safe for beverage/food use, and more effectively exhibit the biological activity of each of the AGARICUS BLAZEI MURRILL fruiting body and mycelium and chlorella growth factor as compared to each ingredient as a single substance.

DETAILED DESCRIPTION OF THE INVENTION

Figure 1:
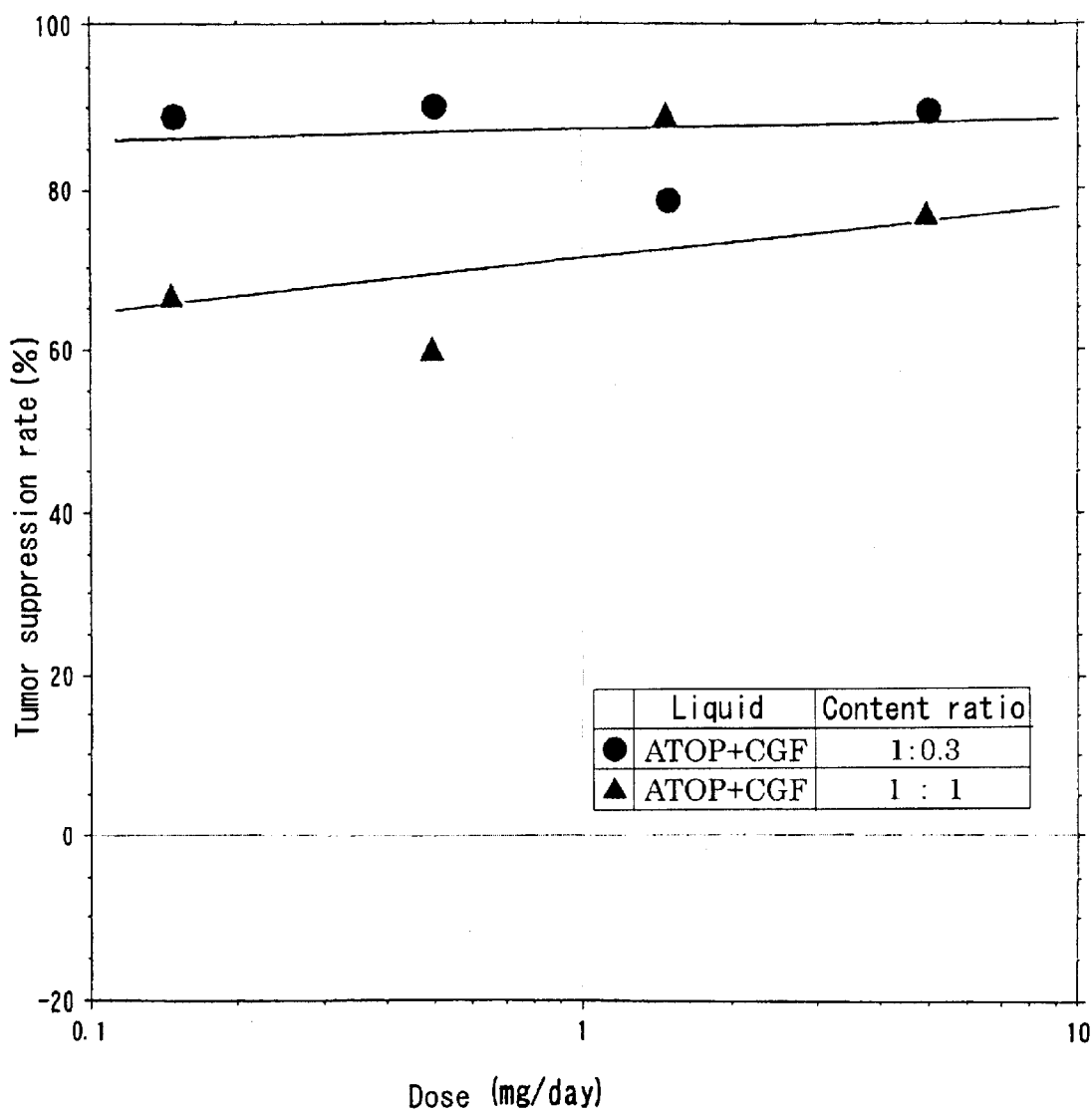
FIG. 1 is a graph showing the relationship between dose and tumor suppression rate for two combinations of a mixture of the AGARICUS BLAZEI MURRILL fruiting body and mycelium extract, and chlorella growth factor, in different ratios by dry weight.

It is preferable that the AGARICUS BLAZEI MURRILL fruiting body used for the present invention have its cell wall destroyed previously. In addition, the AGARICUS BLAZEI MURRILL mycelium extract used is preferably prepared by removing the mycelium from a culture broth of the AGARICUS BLAZEI MURRILL mycelium by centrifugation or filtration. This extract may, for example, be used as an appropriately concentrated liquid, or as a dry powder. Although the mixture of the AGARICUS BLAZEI MURRILL fruiting body and mycelium extract in the present invention may be used as a dry powder of a mixture of the mycelium with its cell wall destroyed previously and a mycelium extract, no other modes of its use are to be construed as useless.

The mixture of the AGARICUS BLAZEI MURRILL fruiting body and mycelium extract used may be such that the ratio by dry weight of the fruiting body and mycelium extract is 1:0.05 to 1:0.5. Preferably, the ratio by dry weight of the AGARICUS BLAZEI MURRILL fruiting body and mycelium extract is 1:0.1 to 1:0.2, more preferably 1:0.18.

The chlorella growth factor for the present invention can, for example, be obtained by heating a concentrate of a single-cell green alga belonging to the genus CHLORELLA, such as *CHLORELLA PYRENOIDOSA, CHLORELLA ELLIPSOIDEA, CHLORELLA VULGARIS,* or *CHLORELLA REGULARIS,* preferably *CHLORELLA PYRENOIDOSA,* extracting the water-soluble components, and removing the insoluble solid contents by solid-liquid separation. This substance may be used as an appropriately concentrated liquid, or as a dry powder. For the present invention, a chlorella growth factor exhibiting an OD value at 260 nm wavelength of 4000 to 6000 in a dry powder form (value obtained by determining the ultraviolet absorbance at 260 nm wavelength of a solution of chlorella growth factor in a dry powder form in a 7500-fold quantity by weight of water using a spectrometer, and multiplying by 7500) can preferably be used. More preferably, the chlorella growth factor is a chlorella growth factor exhibiting an OD value at 260 nm wavelength of 4500 to 5500 in a dry powder form, and still more preferably a chlorella growth factor exhibiting an OD value at 260 nm wavelength of 4900 to 5100 in a dry powder form, and containing a chlorella growth factor exhibiting an OD value at 260 nm wavelength of $50 \times 10^2$ in a dry powder form.

The mixture of the AGARICUS BLAZEI MURRILL fruiting body and mycelium extract in the present invention may be used, for example, in the form of a powder, or a solution or a dispersion in a liquid for drinking such as water.

The ratio by dry weight of the mixture of the AGARICUS BLAZEI MURRILL fruiting body and mycelium extract, and chlorella growth factor, in the present invention is 1:0.05 to 1:1. The ratio by dry weight of the mixture of the AGARICUS BLAZEI MURRILL fruiting body and mycelium extract, and chlorella growth factor, is preferably 1:0.1 to 1:0.5, more preferably 1:0.2 to 1:0.4, and still more preferably 1:0.3. The content ratio is preferably determined on the basis of a chlorella growth factor exhibiting an OD value at 260 nm wavelength of 5000 in a dry powder form. When using a chlorella growth factor exhibiting an OD value at 260 nm wavelength of other than 5000 in a dry powder form, the ratio by dry weight of chlorella growth factor to the mixture of the AGARICUS BLAZEI MURRILL fruiting body and mycelium extract may have a value inversely proportional to the OD value at 260 nm wavelength in a dry powder form (e.g., 1:0.6 for 2500 OD value, provided that the base OD value is 5000 and the base ratio by dry weight is 1:0.3).

When the composition for drinking/eating of the present invention in solution or dispersion in physiological saline was orally administered by gavage at a dose of 7500 mg/kg to Crj:CD(SD)IGS(SPF) rats (males weighing 100 to 160 g and females weighing 80 to 130 g) at 5 weeks of age, no animals died, nor was there any abnormal finding in any animal. The composition for drinking/eating of the present invention was thus confirmed as very safe, with an acute toxicity LD50 exceeding 7500 mg/kg.

The composition for drinking/eating of the present invention can, for example, be taken at a dose of 0.05/kg to 0.2 g/kg per day by an adult, based on dry weight, as is or in containment in a beverage/food.

The beverage/food of the present invention, which contains the composition for drinking/eating of the present invention, is exemplified by various processed foods, confectionery, and soft drinks.

EXAMPLES

The present invention is hereinafter described in more detail by means of the following examples, which are not to be construed as limitative.

Example 1

A dry powder of a mixture of the AGARICUS BLAZEI MURRILL (hime-matsutake Iwade 101 strain) fruiting body with its cell wall destroyed previously and mycelium extract (ratio by dry weight of fruiting body and mycelium extract= 1:0.18) [trade name: ATOP, produced by Powerful Kenko Shokuhin] 20 parts by weight
Powdered chlorella growth factor (prepared by dry-powdering the water-soluble components of a thermal extract of a concentrate of CHLORELLA PYRENOIDOSA, exhibiting an OD value at 260 nm wavelength of $50 \times 10^2$ in a dry powder form) [trade name: Chlorella C.G.F W-5000, produced by Sun Chlorella] 6 parts by weight (dry weight)

The above ingredients were dissolved and dispersed in water for injection (trade name: Otsuka Distilled Water, produced by Otsuka Pharmaceutical Factory) to yield Example liquid 1 (ATOP:CGF=1:0.3) at four concentrations.

Example 2

A dry powder of a mixture of the AGARICUS BLAZEI MURRILL (hime-matsutake Iwade 101 strain) fruiting body with its cell wall destroyed previously and mycelium extract (ratio by dry weight of fruiting body and mycelium extract= 1:0.18) [trade name: ATOP, produced by Powerful Kenko Shokuhin] 13 parts by weight
Powdered chlorella growth factor (prepared by dry-powdering the water-soluble components of a thermal extract of a concentrate of CHLORELLA PYRENOIDOSA, exhibiting an OD value at 260 nm wavelength of $50 \times 10^2$ in a dry powder form) [trade name: Chlorella C.G.F W-5000, produced by Sun Chlorella] 13 parts by weight (dry weight)

The above ingredients were dissolved and dispersed in water for injection (trade name: Otsuka Distilled Water, produced by Otsuka Pharmaceutical Factory) to yield Example liquid 2 (ATOP:CGF=1:1) at the same four concentrations as in Example 1.

Comparative Example 1

26 parts by weight of a dry powder of a mixture of the AGARICUS BLAZEI MURRILL (hime-matsutake Iwade 101 strain) fruiting body with its cell wall destroyed previously and mycelium extract (ratio by dry weight of fruiting body and mycelium extract=1:0.18) was dissolved and dispersed in water for injection (trade name: Otsuka Distilled Water, produced by Otsuka Pharmaceutical Factory) to yield Comparative example liquid 1 (ATOP) at the same four concentrations as in Example 1.

Comparative Example 2

26 parts by weight (dry weight) of powdered chlorella growth factor (prepared by dry-powdering the water-soluble components of a thermal extract of a concentrate of CHLORELLA PYRENOIDOSA, exhibiting an OD value at 260 nm wavelength of $50 \times 10^2$ in a dry powder form) [trade name: Chlorella C.G.F W-5000, produced by Sun Chlorella] was dissolved and dispersed in water for injection (trade name: Otsuka Distilled Water, produced by Otsuka Pharmaceutical Factory) to yield Comparative example liquid 2 (CGF) at the same four concentrations as in Example 1.

Antitumor Effect Test

Using the mouse mammary gland adenocarcinoma 755 [Ca755], a mouse tumor line excellent in clinical predictability, in vivo anti-tumor effects in the animal body were examined.

Male Slc:BDF$_1$ mice at 5 weeks of age were acclimated (including 1 week of quarantine), after which animals free from abnormal gross findings were selected. The weights of the animals ranged from 18.6 to 24.2 g at the time of test initiation.

The animals were housed as 10-member groups in polysulfone cages (265 mm width×427 mm length×204 mm height) attached to a mobile stainless steel rack (1790 mm width×470 mm length×1650 mm height) under environmental conditions involving a temperature of 22±3° C., a humidity of 50±20%, lighting for 12 hours (8:00–20:00), and a ventilation frequency of 13 to 17 times/hour throughout the acclimation and test periods. Seventeen groups were established, and each mouse had free access to a pellet food (trade name: Lab MR Stock, produced by Nihon Nosan Kogyo) from a stainless steel pellet food feeder. For drinking water, tap water was given from a polysulfone watering device (with stainless steel tip) ad libitum.

To each mouse in the 17 groups at 6 weeks of age, tumor cells obtained by 10 to 14 days of subculture in the C57BL/6 mouse were transplanted by subcutaneous injection in the flank in a ratio of $1 \times 10^5$ cells/0.05 mL(milliliter)/mouse (Day 0).

Starting on the day after transplantation, each of Example liquid 1 (ATOP:CGF=1:0.3) at the aforementioned four concentrations, Example liquid 2 (ATOP:CGF=1:1) at the aforementioned four concentrations, Comparative example liquid 1 (ATOP) at the aforementioned four concentrations, and Comparative example liquid 2 (CGF) at the aforementioned four concentrations was orally administered to the 17 groups in an amount of 0.4 mL(milliliter)/mouse once daily for 14 consecutive days. The doses of the Example liquids and Comparative example liquids at the respective concentrations were 0.15 mg(milligram)/mouse/day, 0.5 mg/mouse/day, 1.5 mg/mouse/day, and 5 mg/mouse/day, respectively. For the control group, the same water for injection as that used in Example liquid 1 was orally administered in an amount of 0.4 mL(milliliter)/mouse once daily for 14 consecutive days.

On the day after completion of administration (Day 15), each mouse had its cervical vertebra dislocated under ether anesthesia, and the tumor was extirpated and weighed in a wet state. The results are shown in FIGS. 1 and 2.

FIG. 1 shows the relationship between dose and tumor suppression rate for two combinations of a mixture of the AGARICUS BLAZEI MURRILL fruiting body and mycelium extract, and chlorella growth factor, in different ratios by dry weight. FIG. 2 shows the relationship between dose and tumor suppression rate in animals receiving a liquid containing a composition comprising a mixture of the AGARICUS BLAZEI MURRILL fruiting body and mycelium extract, and chlorella growth factor, animals receiving a liquid containing a mixture of the AGARICUS BLAZEI MURRILL fruiting body and mycelium extract alone, and animals receiving a liquid containing chlorella growth factor alone. In FIGS. 1 and 2, the abscissa indicates the common logarithm of dose (mg/day), and the ordinate indicates tumor suppression rate (%). Tumor suppression rate is obtained using the equation: [1−(wet weight of tumor from each liquid administration group)/(wet weight of tumor from control group)]×100%.

Figure 2:
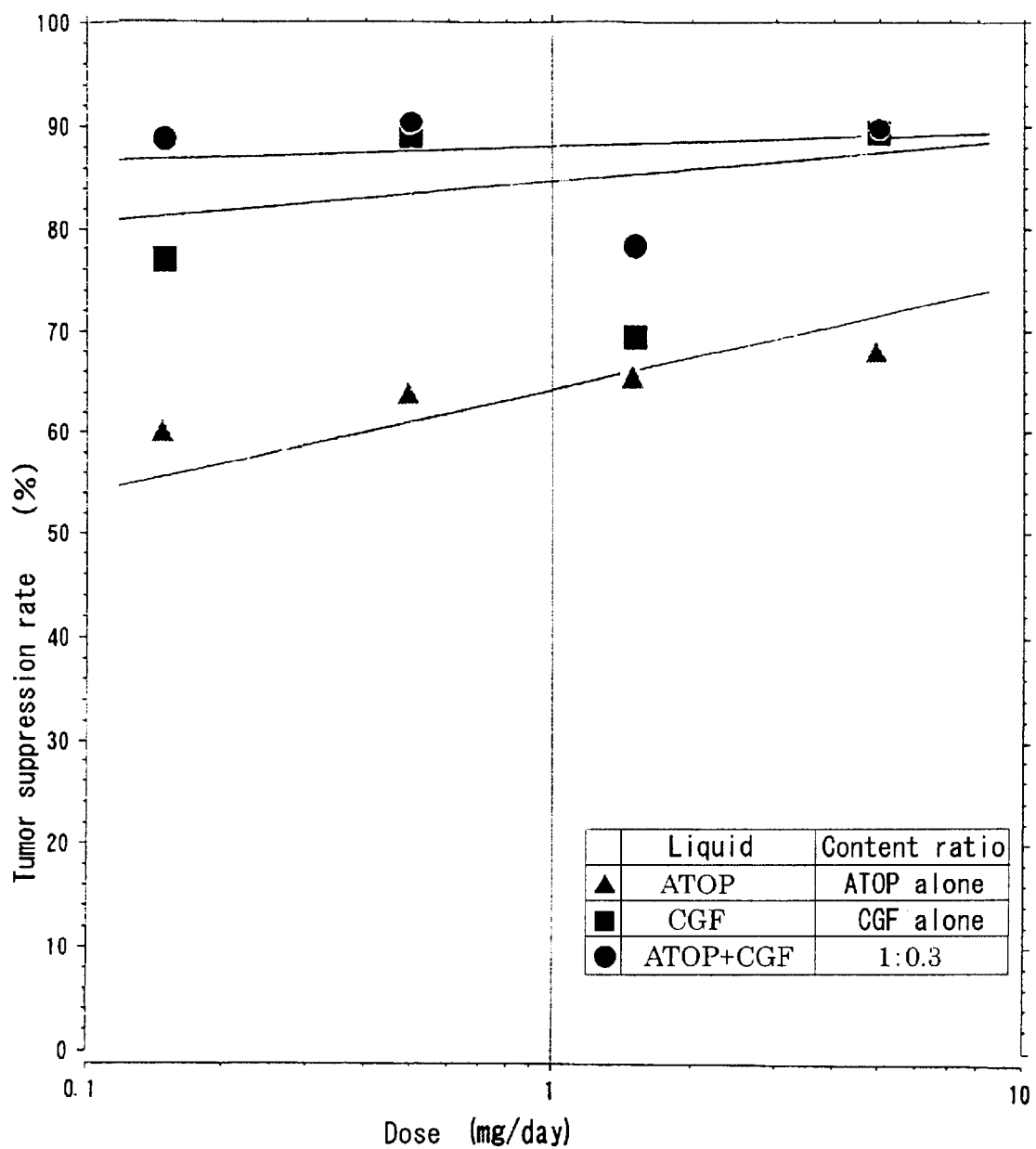
FIG. 2 is a graph showing the relationship between dose and tumor suppression rate in animals receiving a liquid containing a composition comprising a mixture of the AGARICUS BLAZEI MURRILL fruiting body and mycelium extract, and chlorella growth factor, and animals receiving each of said mixture and chlorella growth factor alone.

From FIGS. 1 and 2, it is evident that Example liquid 1 (ATOP:CGF=1:0.3) had the most potent tumor suppression effect, followed by Example liquid 2 (ATOP:CGF=1:1); the tumor suppression effects of Example liquid 1 (ATOP:CGF=1:0.3) and Example liquid 2 (ATOP:CGF=1:1) were found to significantly surpass those of Comparative example liquid 1 (ATOP) and Comparative example liquid 2 (CGF).

What is claimed is:

1. Composition for drinking/eating comprising a mixture of the AGARICUS BLAZEI MURRILL fruiting body and mycelium extract in a ratio by dry weight of 1:0.05 to 1:0.5, and chlorella growth factor, wherein the ratio by dry weight of said mixture and chlorella growth factor is 1:0.05 to 1:1.

2. The composition for drinking/eating of claim 1 wherein the ratio by dry weight of said AGARICUS BLAZEI MURRILL fruiting body and mycelium extract is 1:0.1 to 1:0.2.

3. The composition for drinking/eating of claim 2 wherein the ratio by dry weight of said mixture of the AGARICUS BLAZEI MURRILL fruiting body and mycelium extract, and chlorella growth factor, is 1:0.1 to 1:0.5.

4. The composition for drinking/eating of claim 2 wherein the ratio by dry weight of said mixture of the AGARICUS BLAZEI MURRILL fruiting body and mycelium extract, and chlorella growth factor, is 1:0.2 to 1:0.4.

5. The composition for drinking/eating of claim 2 wherein the ratio by dry weight of said mixture of the AGARICUS BLAZEI MURRILL fruiting body and mycelium extract, and chlorella growth factor, is 1:0.3.

6. The composition for drinking/eating of claim 2 wherein said AGARICUS BLAZEI MURRILL fruiting body is a fruiting body with its cell wall destroyed previously.

7. The composition for drinking/eating of claim 2 wherein said chlorella growth factor is a chlorella growth factor exhibiting an OD value at 2.60 nm wavelength of 4000 to 6000 in a dry powder form.

8. The composition for drinking/eating of claim 2 wherein said chlorella growth factor is a chlorella growth factor exhibiting an OD value at 250 nm wavelength of 4500 to 5500 in a dry powder form.

9. The composition for drinking/eating of claim 2 wherein said chlorella growth factor is a chlorella growth factor exhibiting an OD value at 260 nm wavelength of 4900 to 5100 in a dry powder form.

10. The composition for drinking/eating of claim 1 wherein the ratio by dry to weight of said AGARICUS BLAZEI MURRILL fruiting body and mycelium extract is 1:0.18.

11. The composition for drinking/eating of claim 1 wherein the ratio by dry weight of said mixture of the AGARICUS BLAZEI MURRILL fruiting body and mycelium extract, and chlorella growth factor, is 1:0.1 to 1:0.5.

12. The composition for drinking/eating of claim 11 wherein said AGARICUS BLAZEI MURRILL fruiting body is a fruiting body with its cell wall destroyed previously.

13. The composition for drinking/eating of claim 11 wherein said chlorella growth factor is a chlorella growth factor exhibiting an OD value at 2.60 nm wavelength of 4000 to 6000 in a dry powder form.

14. The composition for drinking/eating of claim 1 wherein the ratio by dry weight of said mixture of the AGARICUS BLAZEI MURRILL fruiting body and mycelium extract, and chlorella growth factor, is 1:0.2 to 1:0.4.

15. The composition for drinking/eating of claim 1 wherein the ratio by dry weight of said mixture of the AGARICUS BLAZEI MURRILL fruiting body and mycelium extract, and chlorella growth factor, is 1:0.3.

16. The composition for drinking/eating of claim 1 wherein said AGARICUS BLAZEI MURRILL fruiting body is a fruiting body with its cell wall destroyed previously.

17. The composition for drinking/eating of claim 1 wherein said chlorella growth factor is a chlorella growth factor exhibiting an OD value at 2.60 nm wavelength of 4000 to 6000 in a dry powder form.

18. The composition for drinking/eating of claim 1 wherein said chlorella growth factor is a chlorella growth factor exhibiting an OD value at 250 nm wavelength of 4500 to 5500 in a dry powder form.

19. The composition for drinking/eating of claim 1 wherein said chlorella growth factor is a chlorella growth factor exhibiting an OD value at 260 nm wavelength of 4900 to 5100 in a dry powder form.

20. A beverage/food containing the composition for drinking/eating of claim 1.

* * * * *